United States Patent [19]

Cleveland et al.

[11] Patent Number: 5,231,674
[45] Date of Patent: Jul. 27, 1993

[54] EYE TRACKING METHOD AND APPARATUS

[75] Inventors: Dixon Cleveland, Vienna; James H. Cleveland, Clifton; Peter L. Norloff, Fairfax, all of Va.

[73] Assignee: LC Technologies, Inc., Fairfax, Va.
[21] Appl. No.: 702,139
[22] Filed: May 13, 1991

Related U.S. Application Data

[63] Continuation of Ser. No. 363,873, Jun. 9, 1989, abandoned.
[51] Int. Cl.$^5$ .................. G06K 9/48; G06K 9/20; A61B 3/14
[52] U.S. Cl. .................. 382/6; 382/22; 382/48; 351/210
[58] Field of Search ............ 382/49, 29, 27, 22, 382/6, 54, 9, 48; 351/210, 209

[56] References Cited

U.S. PATENT DOCUMENTS

| | | | |
|---|---|---|---|
| 3,525,565 | 8/1970 | O'Neill et al. | 351/7 |
| 3,533,683 | 10/1970 | Stark et al. | 351/6 |
| 3,533,684 | 10/1970 | Stark et al. | 351/6 |
| 3,804,496 | 4/1974 | Crane et al. | 351/6 |
| 3,864,030 | 2/1975 | Cornsweet | 351/210 |
| 3,869,694 | 3/1975 | Merchant et al. | 367/117 |
| 4,003,642 | 1/1977 | Vogeley | 351/6 |
| 4,034,401 | 7/1977 | Mann | 358/93 |
| 4,199,785 | 4/1980 | McCullough et al. | 358/180 |
| 4,231,066 | 10/1980 | Merchant | 358/180 |
| 4,251,139 | 2/1981 | Matsumura | 351/7 |
| 4,287,410 | 9/1981 | Crane et al. | 250/201 |
| 4,373,787 | 2/1983 | Crane et al. | 351/210 |
| 4,544,246 | 10/1985 | Crane et al. | 351/211 |
| 4,595,990 | 1/1986 | Garwin et al. | 364/518 |
| 4,626,089 | 12/1986 | Takahashi et al. | 351/208 |
| 4,635,203 | 1/1987 | Merchant | 364/458 |
| 4,648,052 | 3/1987 | Friedman et al. | 364/550 |
| 4,673,264 | 6/1987 | Takahashi | 351/211 |
| 4,678,297 | 7/1987 | Ishikawa et al. | 351/208 |
| 4,695,959 | 9/1987 | Lees et al. | 364/458 |
| 4,725,722 | 2/1988 | Maeda et al. | 250/201 |
| 4,755,045 | 7/1988 | Borah et al. | 351/210 |
| 4,756,613 | 7/1988 | Okashita | 351/206 |
| 4,789,235 | 12/1988 | Borah et al. | 351/246 |
| 4,809,342 | 2/1989 | Kappner | 382/32 |
| 4,959,714 | 9/1990 | Lo et al. | 382/22 |
| 4,977,504 | 12/1990 | Funahashi | 382/6 |
| 5,016,282 | 5/1991 | Tomono et al. | 382/2 |

FOREIGN PATENT DOCUMENTS 57-19882  2/1982  Japan .................. 382/48

OTHER PUBLICATIONS

A. Downing, "Eye Controlled and Other Fast Communicators for Speech Impaired and Physically Handicapped Persons", *Australasian Phys. & Engg. Scis in Med.* vol. 8, No. 1, pp. 17–21 (1985).
J. Levine et al., "Performance of an Eyetracker for Office Use", *Comput. Biol. Med.* vol. 14, No. 1, pp. 77–89 (1984).
J. Merchant et al., "A Remote Oculometer Permitting Head Movement", Report No. AMRL-TR-73-69, Aerospace Medical Research Laboratory, Air Force Systems Command. Dayton, Ohio (Oct. 1973).
L. Young et al., "Survey of Eye Movement Recording Methods", *Behavior Resear Methods and Instrumentation*, vol. 7, No. 5, pp. 397–429 (1975).
M. Friedman et al., "The Eyetracker Communication System", John Hopkins APL Technical Digest vol. 3, No. 3, pp. 250–252 (1982).
R. Razdan et al., "Eye Tracking for Man/Machine Interfaces", Sensors, pp. 39 42 ff (Sep. 1988).
Anon., "ISCAN® Eye Movement Monitoring and Pupillometry Systems 1988-89 Catalogue", ISCAN Inc. (1986).
Anon., "eye-trac ®: Field Proven Systems for Quantitative Analysis of Eye Movement, Pupillometry, and Visual Function", Applied Science Laboratori (1982).

*Primary Examiner*—David K. Moore
*Assistant Examiner*—Michael Cammarata
*Attorney, Agent, or Firm*—Kirkland & Ellis

[57] ABSTRACT

In applications where it is desired to determine the locations of image features, such as eye monitoring to determine the direction that a person is gazing, determining the point at which he is gazing, or measuring the motions of his eye using a camera to capture an optical image of the eye and image processing to extract information about the eye's gaze point and/or orientation, there is provided a method and apparatus for precise location of image features such as edge coordinates between the pupil anc iris of the eye and of the center coordinates of light reflections off the cornea of the eye.

18 Claims, 7 Drawing Sheets

EYE TRACKING METHOD AND APPARATUS

This is a continuation of co-pending application Ser. No. 07/363,873 filed on Jun. 9, 1989, now abandoned.

BACKGROUND

The invention relates to methods for locating image features.

In eyegaze technology it has long been known that the angular orientation of the optical axis of the eye can be measured remotely by the corneal reflection method. The method takes advantage of the eye's properties that the surface of the cornea is very nearly spherical over about an 11-to-15-degree cone around the eye's optic axis, and the relative locations of the pupil and a reflection of light from the cornea, e.g., the first Purkinje image, change in proportion to eye rotation. The corneal reflection method for determining the orientation of the eye is described in U.S. Pat. No. 3,864,030 to Cornsweet: U.S. Pat. No. 3,869,694 to Merchant et al.: U.S. Pat. Nos. 4,287,410 and 4,373,787 to Crane et al.: U.S. Pat. No. 4,648,052 to Friedman et al.: and U.S. Pat. Nos. 4,755,045 and 4,789,235 to Borah et al; A. R. Downing, "Eye Controlled and Other Fast Communicators for Speech Impaired and Physically Handicapped Persons," Australasian Phys. Eng. Scis. in Med. vol. 8, no. 1, pp. 17–21 (1985): J. L. Levine, "Performance of an Eyetracker for Office Use," Comput. Biol. Med., vol. 14, no. 1, pp. 77–89 (1984): and J. Merchant et al., "A Remote Oculometer Permitting Head Movement," Rpt. No. AMRL-TR-73-69, Contr. No. F33615-72-C-1038, U.S. Air Force Systems Command (1973), as well as U.S. Pat. No. 4,034,401 to Mann: and U.S. Pat. No. 4,595,990 to Garwin et al., and certain U.S. Pat. Applications of Thomas E. Hutchinson, Ser. No. 07/086,809 now U.S. Pat. No. 4,836,670; Ser. No. 07/326,787 now U.S. Pat. No. 4,973,149; and Ser. No. 07/267,266 now U.S. Pat. No. 4,950,069.

A typical equipment configuration for an eye orientation monitor 10 is shown in FIG. 1. The hardware generally includes a video camera 12 and lens 14 to observe eye 16, a light source 18 such as a near-infrared-emitting diode near or on the lens to illuminate the eye, a digital frame grabber 20 to capture the video image from camera 12 and put it into a computer readable form, and a general purpose digital computer 22 to perform image processing and mathematical computations. The outputs of the camera 12 and/or computer 22 may also be displayed on a suitable monitor 24.

Fundamentally, the corneal reflection method comprises the following steps: processing the image of the eye to detect and locate the center of the corneal reflection or first Purkinje image processing the image to detect and locate the center of the pupil: computing the 2-dimensional vector between the center of the pupil and the center of the corneal reflection: and computing the 2-dimensional angular orientation of the eye with respect to the camera axis from the pupil-center/corneal-reflection vector. Naturally, the accuracy with which the eye's angular orientation and gaze point can be computed is heavily influenced by the accuracies with which the centers of the pupil and corneal reflection are computed.

Typically the image of the corneal reflection formed by camera 12 is a small cluster of high intensity picture elements (pixels). A simple method for finding the center of the corneal reflection is peak detection where the position of the peak image intensity is taken to be the location of the corneal reflection. In practice, however, noise and pixel amplitude clipping often render the peak detection method unreliable. Camera noise can cause the peak amplitude pixels to be far from the actual center of the corneal reflection. Also, the amplitude of the camera's image of the corneal reflection is often clipped because its intensity exceeds the linear range of the camera sensor: thus, several neighboring pixels will have equal, i.e., the maximum, intensities.

One method for reducing the effects of noise and clipping is to set a corneal reflection detection threshold valve $T_{cr}$ and compute the simple average or centroid of the coordinates of all pixels whose intensities exceed the threshold. The pixel coordinates $x_{cr}, y_{cr}$ of the corneal reflection are thus given by:

$$x_{cr} = \frac{1}{N} \sum_{n=1}^{N} x_n$$

$$y_{cr} = \frac{1}{N} \sum_{n=1}^{N} y_n$$

where N is the total number of pixels that exceed the corneal reflection threshold, n is an index of those pixels, and x and y are the coordinates of those pixels in the camera image. This method can be referred to as the "equal-weighting" method because any pixel that exceeds the threshold is given an equal weight in estimating the corneal reflection position.

The center of the pupil is typically found by locating several points on the edge of the pupil, then computing the pupil center coordinates from the edge coordinates. Using an amplitude threshold crossing technique as just described, the edge coordinates are located where the image intensity crosses a pupil detection threshold value $T_p$ set somewhere between the average intensity of the pupil and the average intensity of the iris. The horizontal coordinate of the pupil center can be estimated, for example, by averaging the left and right edge coordinates of one or more horizontal "cuts" through the pupil, and the vertical coordinate of the pupil center can be similarly estimated by averaging the top and bottom edge coordinates of one or more vertical cuts through the pupil. Another way to find the pupil center is to fit a circle or ellipse to the detected edge coordinates and mathematically compute the center of the fitted circle or ellipse.

In certain orientations of the eye, the corneal reflection lies on or near the edge of the pupil and can disrupt the pupil edge detection procedure. The pupil location procedure should use information about the position of the corneal reflection to avoid attempting pupil edge detection in the region of the corneal reflection.

As described above, prior image processing methods locate the pupil within the camera image by detecting the difference in intensities between the pupil and the surrounding iris. In the usual image of the eye, the pupil appears to be darker than the surrounding iris since more light reflects from the iris than enters the pupil and reflects from the inner eye. This is commonly known as the "dark-pupil" or "dark-eye" effect. Typically, the relative intensities of the iris and pupil are not sufficiently different to make the image processing easy. Alternative methods were sought to increase the contrast ratio between the pupil and its surrounding iris.

The retinas of most eyes are highly reflective. As illustrated in FIG. 2a, the light source 18 is directed at eye 16, and the eye's lens 16-1 causes the light that enters pupil 16-2 to converge to a point on retina 16-3. As illustrated in FIG. 2b, some of the light that reflects from the retina passes back out through the pupil and is partially refocused by lens 16-1 in such a way that it is directed primarily back toward the light source. In flash photography, if the flash lamp is too close to the lens, a significant portion of this reflected light enters the camera lens aperture, producing pictures of people with bright pupils. The phenomenon was therefore named the "bright-eye" or "bright-pupil" effect. The bright-eye effect is avoided in flash photograph by moving the flash unit away from the camera lens axis to minimize the amount of reflected light entering the camera lens.

While the bright-eye effect is generally undesirable in most photography, it is useful in optical eye monitoring applications. If, as illustrated in FIGS. 3a and 3b, the light source 18 used to generate the corneal reflection is either mounted coaxially with the camera lens (see FIG. 3a) or disposed with respect to a beam-splitter 26 so as to appear coaxial with the lens (see FIG. 3b), the bright-pupil effect is maximized. If the light source is bright enough, e.g., by use of a lens 18-1 shown in FIG. 3b, the contrast ratio between the iris and the bright pupil in the camera image can be made significantly greater than the contrast ratio between the iris and a dark pupil. With the improved contrast ratio, image processing routines can locate the pupil edges and center more reliably and accurately.

Locating the pupil center and corneal reflection is important because once the coordinates of the centers of the pupil and corneal reflections have been determined, the 2-dimensional vector between the two points can be computed as the difference between the two points:

$$dx = x_p - x_{cr}$$

$$dy = y_p - y_{cr}$$

where $x_p$ and $y_p$ are the pupil center coordinates within the camera frame of reference, $x_{cr}$ and $y_{cr}$ are the corneal center coordinates within the camera frame of reference, and dx and dy comprise the 2-dimensional pupil-center/corneal-reflection vector's components.

For example (see FIG. 4), let the pitch and yaw angles $\theta$ and $\psi$, respectively, of the eye's orientation be defined with respect to the camera axis. (It will be understood that if it is desired to express the eye's orientation with respect to other coordinate frames, the desired angles may be computed by straightforward mathematical transformations relating the camera coordinate frame to the desired coordinate frame.) Further, let $\theta$ and $\psi$ be defined with respect to the eye's optical axis defined as passing through the center of the pupil and being normal to the optical plane of the eye's lens. The optical axis of the eye is different from its visual axis which also passes through the pupil center, but is further defined as passing through the center of the foveola, i.e., that part of the retina where a person focuses his visual concentration. Physiologically, the foveola generally lies somewhere to the person's lateral side of the point where the optical axis intercepts the retina; thus, the visual axis is rotated from the optical axis by an angle $\epsilon$ of about 2 degrees to 8 degrees horizontally (yaw) and an angle $\gamma$ of about $\pm 3$ degrees vertically (pitch). Since the camera's view of the corneal reflection is based on the geometry of the eye's lens and not on the position of the foveola, it is convenient in the image processing domain to work in terms of the eye's optical axis rather than its visual axis. If it is desired to know the orientation of the eye's visual axis, the eye's optical axis pitch and yaw angles $\theta$ and $\psi$ can be adjusted by the angular difference between the eye's optical and visual axes.

FIG. 4 shows a side schematic view of the camera looking at eye 16. Within the camera, the camera's sensor plane 12-1 is a distance s from lens plane 14-1. In the following description, the light source that illuminates the eye is assumed to be located at the center of the camera lens. The location of eye 16 in the camera coordinate frame can be defined in terms of a range R along the camera axis from the camera lens to the center of the pupil and a corneal offset angle $\alpha_{cr}$ between the camera axis and the center of the corneal reflection. Similarly, an angle $\alpha_p$ is the angle between the camera axis and the pupil center. A line from the center of the eye's pupil through the center of the camera lens is called the pupil ray. An extension of the pupil ray through the camera lens intercepts the camera sensor plane at the point $y_p$. By the law of optical reflection, the corneal reflection lies on the cornea at the point where the cornea surface is normal to the center of the camera lens because the light source is located there. The line from the corneal reflection through the center of the camera lens is called the corneal reflection ray. An extension of the corneal reflection ray through the camera lens intercepts the camera sensor plane at the point $y_{cr}$. It can also be noted that an extension of the corneal reflection ray in the opposite direction passes through the cornea's center of curvature.

A procedure for computing the eye's orientation or pitch angle $\theta$ is as follows. An angle $\eta$ between the corneal reflection ray and the eye's optical axis is the sum of the corneal offset angle $\alpha_{cr}$ and the eye's optical axis orientation angle $\theta$:

$$\eta = \alpha_{cr} + \theta$$

The corneal offset angle $\alpha_{cr}$ can be calculated from the corneal reflection position $y_{cr}$ on the sensor plane 12-1 and the distance s:

$$\alpha_{cr} = arctan\,(y_{cr}/s)$$

As defined above, the distance dy on the camera sensor plane is the difference between the measured pupil center $y_p$ and the measured corneal reflection position $y_{cr}$:

$$dy = y_p - y_{cr}$$

By reason of similar triangles, a distance dy', measured parallel to the camera's lens plane, between the actual pupil center and the corneal reflection ray is:

$$dy' = dy\,R/s$$

A distance dy", measured normal to the corneal reflection ray, between the actual pupil center and corneal reflection ray is:

$$dy'' = dy'\,cos(\alpha_{cr})$$

Defining the distance from the corneal center of curvature to the pupil center to be $\rho$, the angle $\eta$ is found from dy'':

$$\eta = \arcsin(dy''/\rho)$$

Finally, the eye's optical axis pitch angle $\theta$ is:

$$\theta = \eta - \alpha c_{cr}$$

Using small-angle approximations, the above equations combine and reduce to:

$$\theta \simeq (R/\rho s)\{y_p(1-\rho/R) - y_{cr}\}$$

and since the distance $\rho$ between the corneal center of curvature and the pupil center is small with respect to the range R from the camera lens to the eye, the pitch angle approximation can be further simplified to:

$$\theta \simeq (R/\rho s)(y_p - y_{cr}) = (R/\rho s)dy$$

By similar derivation, the eye's optical axis yaw angle $\psi$ is approximated by:

$$\psi \simeq (R/\rho s)(x_p - x_{cr}) = (R/\rho s)dx$$

last two approximations relate the measured vector components dy and dx to the eye's optical axis orientation angles $\theta$ and $\psi$ with the factor $(R/\rho s)$ as a constant of proportionality.

In some eyegaze tracking applications it is desired to determine the gaze point $(x_g, y_g)$ on a predetermined display plane at which the person is looking. For example, it may be desired to determine where a person is looking on a computer monitor screen or on a printed page. In these applications, a projection is made from the pupil of the eye, along the eye's visual axis, to the intercept point on the display plane. If the display plane is approximately parallel to the camera lens plane, and if the x and y axes of the display plane are approximately parallel to the x and y axes of the camera lens plane, the following derivation shows how to approximate the gaze point from the pupil-center/corneal-reflection vector.

FIG. 5 shows a side schematic view of camera 12, lens 14 and lens plane 14-1, eye 16 and display plane 28. A distance $y_o$ represents the offset of the origin of the display plane with respect to the camera axis, and D is a distance between lens plane 14-1 and display plane 28. From the geometry in FIG. 5, it can be determined that the vertical component $y_g$ of the gaze point is given by:

$$y_g = R \sin(\alpha_p) + (R+D)\sin(\theta+\gamma) - y_o$$

where $\gamma$ is the angle between the eye's optical and visual axes in the pitch plane. Using small-angle approximations and the above approximation of $\theta$, and noting $\alpha_p \simeq y_p/s$ yields:

$$y_g \simeq \frac{R}{s}\left\{\left[\frac{R+D}{\rho} + 1 - \frac{R+D}{R}\right]y_p - \left[\frac{R+D}{\rho}\right]y_{cr}\right\} + \{(R+D)\gamma - y_o\}$$

Since $\{1-(R+D)/R\}$ is much smaller than $(R+D)/\rho$, $y_g$ can be further approximated as:

$$y_g \simeq \{(R+D)R/\rho s\}dy + \{(R+D)\gamma - y_o\}$$

Similarly, the horizontal component of the gaze point may be approximated:

$$x_g \simeq \{(R+D)R/\rho s\}dx + \{(R+D)\epsilon - x_o\}$$

where $\epsilon$ is the angle between the eye's optical and visual axes in the yaw plane, and $x_o$ is the horizontal offset of the origin of the display plane with respect to the camera axis.

In practice, the linearization assumptions introduce errors into the gaze point projection equations: the values of R, D, s, $\rho$, $\gamma$, $\epsilon$, $x_o$ and $y_o$ are difficult to determine accurately: and the display screen is rarely parallel to the camera lens plane. Therefore, explicit calculation of the above gaze point equations is impractical. The form of the equations is highly useful, however, in that they show how the pupil-center/corneal-reflection vector varies with respect to gaze point motions. Keeping the form of the approximations but generalizing the coefficients yields:

$$x_g \simeq a_o + a_x\,dx$$

$$y_g \simeq b_o + b_y\,dy$$

where the a's and b's are generalized, lumped coefficients.

To make it more comfortable for the user to view, it is often desirable to tilt the display plane 28, such as a computer monitor, forward with respect to the camera lens so that the user's view is approximately normal to the plane and the camera "looks up" at the user's eye. Tilt and roll of the display plane can largely be accommodated if the following more general approximations are used:

$$x_g \simeq a_o + a_x\,dx + a_y\,dy + a_{xy}\,dx\,dy$$

$$y_g \simeq b_o + b_x\,dx + b_y\,dy + b_{xy}\,dx\,dy$$

A geometrical analysis of the camera/eye/display configuration shows that the terms, $a_y\,dy$ and $b_x\,dx$ generally compensate for roll of the display screen about the camera's optical axis, and the cross-product terms $a_{xy}\,dx\,dy$ and $b_{xy}\,dx\,dy$ compensate for tilt of the display plane about the camera's pitch and yaw axes respectively.

Values for the generalized coefficients are typically generated by the following calibration procedure: the user sequentially looks at a series of predetermined locations on the display plane 28, the computer measures and records the pupil-center/corneal-reflection vectors for each of those calibration points, and curve fitting methods such as linear regression are used to determine the coefficient values that allow the gaze point equations to generate those calibration points best.

The locations of the predetermined calibration points should be distributed fairly evenly in both dimensions over the display plane 28 where accurate eye-orientation or gaze-point projection is desired. Generally, to get sufficiently accurate coefficient values to achieve adequate gaze-point accuracies, the number of calibration points should be at least twice the number of coefficients used in the prediction equations.

A central goal in most eye monitoring applications is to measure the orientation of the eye with as much accuracy as possible. As described above, the accuracy of the orientation calculations is directly dependent on the accuracy of the measurements of the centers of the pupil and the corneal reflection. In turn, key factors limiting the coordinate measurements of the pupil and corneal reflection centers are the spatial resolution of the digitized image of the eye and amplitude noise on the light intensity samples. It is an objective of the present invention to maximize the accuracy of the pupil center and corneal reflection location measurements in light of the resolution and noise constraints of digital image acquisition, and to carry out those measurements rapidly. It will be appreciated that the advantages of the present invention can be realized in a wide variety of applications, and are obtained in eyegaze tracking using either the dark-eye or bright-eye effect.

SUMMARY

In accordance with the present invention, there is provided a method for computing a coordinate of a point on an edge of an image feature comprising the steps of: collecting a sequence of image intensity samples $q(x_i)$ across the edge: spatially differentiating the sequence to obtain a derivative sequence $dq(x_i)/dx$: obtaining a smoothed derivative sequence $dq_s(x_i)/dx$; subtracting a predetermined threshold value from each element of the smoothed derivative sequence to obtain a thresholded smoothed derivative sequence $dq_t(x_i)/dx$: and computing the coordinate of the point on the edge of the image feature by finding a center of mass of the thresholded smoothed derivative sequence.

In another aspect of the invention, there is provided a method for computing 2-dimensional coordinates of an image feature comprising the steps of: collecting a 2-dimensional group of image intensity sample points $q(x_i,y_j)$, said group including the image feature; subtracting a predetermined threshold value from each sample point in the 2-dimensional group: weighting each quantity produced by the subtracting step by a monotonic function of the positive quantities to obtain a second group of thresholded. weighted intensity sample points $q_t(x_i,y_j)$; and computing the 2-dimensional coordinates of the image feature by finding a center of mass of the second group.

In a further aspect of the invention, there is provided an apparatus for carrying out the methods.

BRIEF DESCRIPTION OF THE DRAWINGS

The various objects and advantages of the present invention will become more apparent after a reading of the following detailed description in conjunction with the drawings in which.

DETAILED DESCRIPTION

Figure 1:
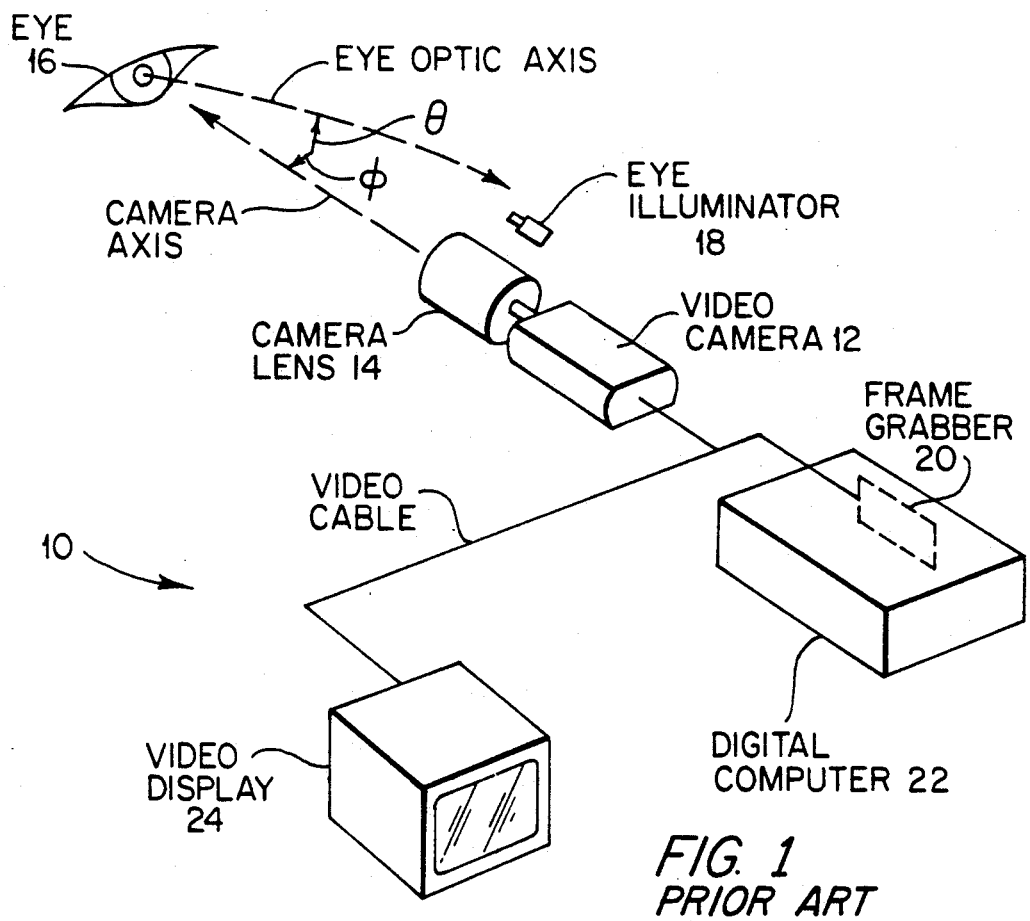
FIG. 1 shows a typical configuration of an eye orientation monitor.
Figure 2A:
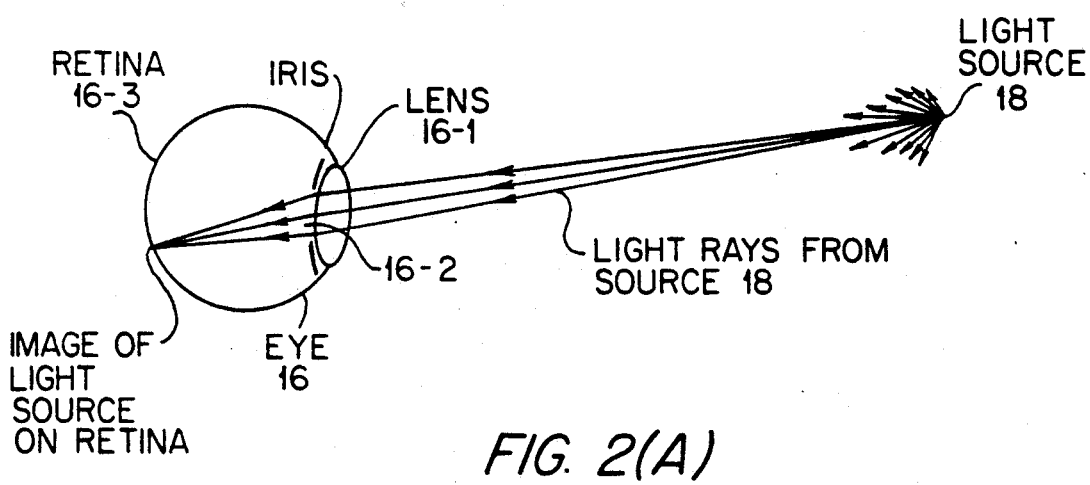
FIGS. 2a and 2b illustrate light propagation leading to the bright-eye effect.
Figure 2B:
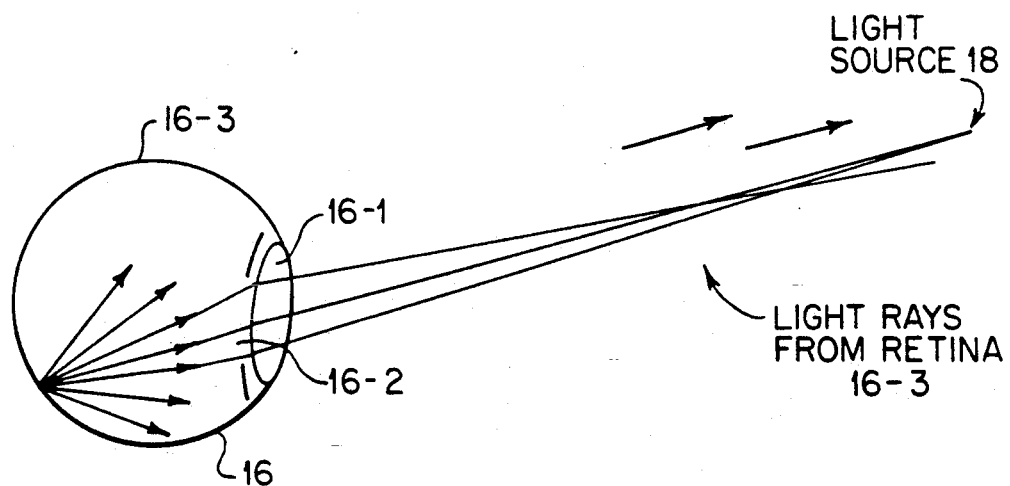
Figure 3A:
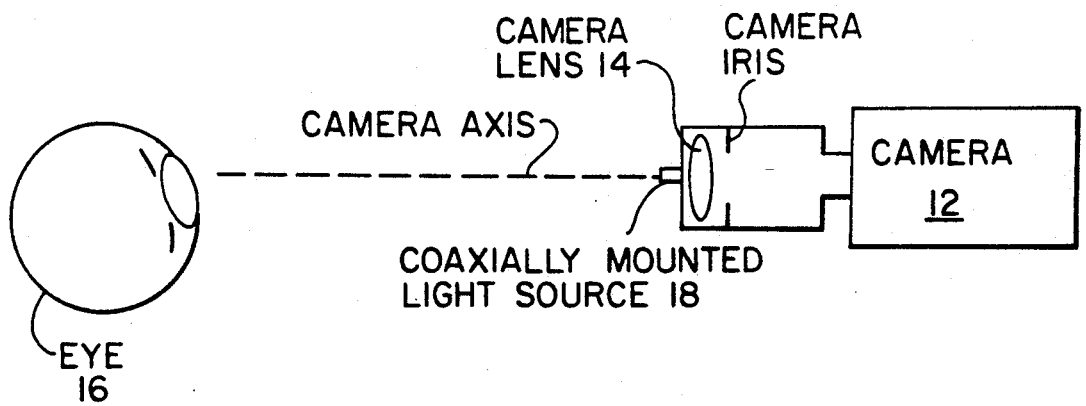
FIGS. 3a and 3b illustrate typical configurations for using the bright-eye effect.
Figure 3B:
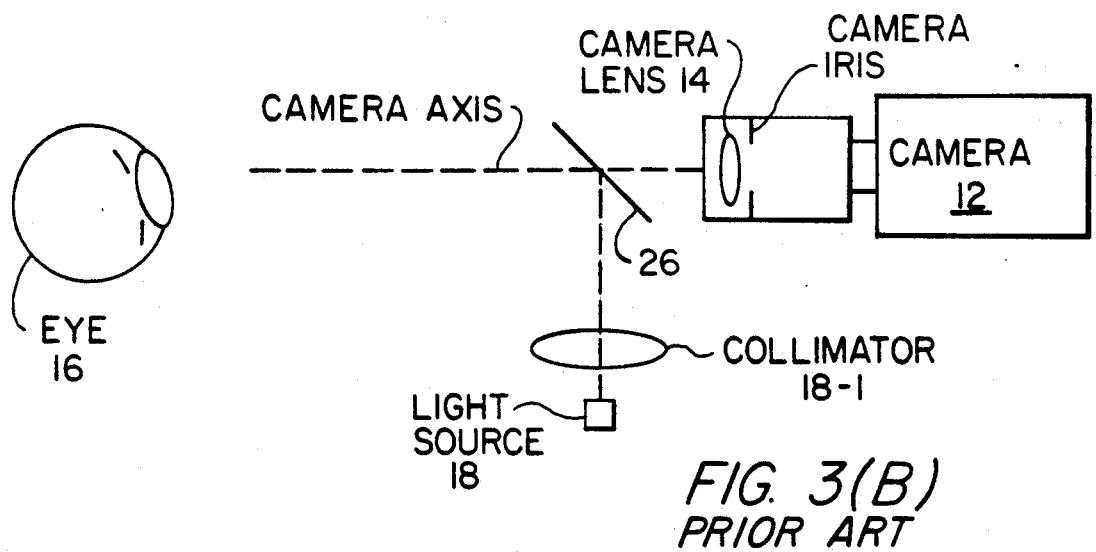
Figure 7A:
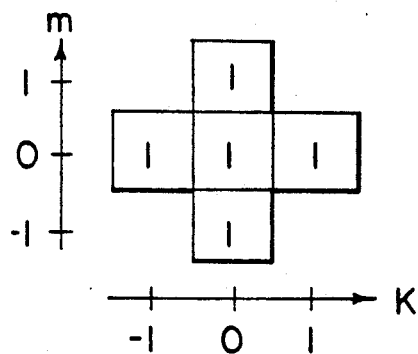
FIGS. 7A-7D show 2-dimensional, symmetric convolution kernels for image smoothing.
Figure 7B:
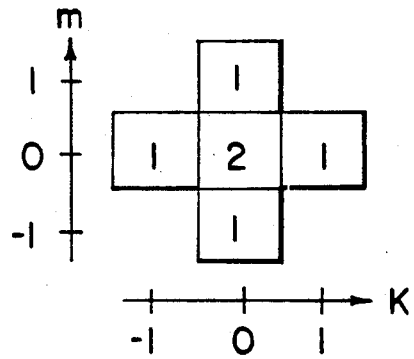
Figure 7C:
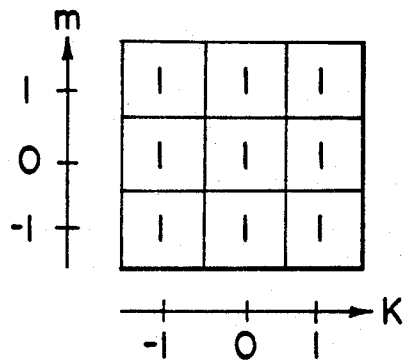
Figure 7D:
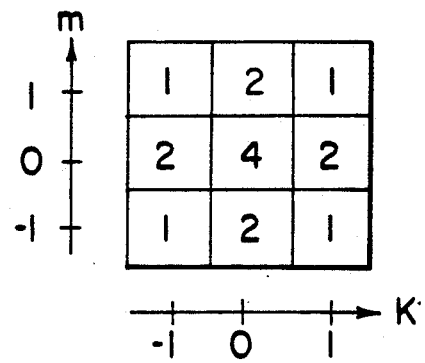
Figure 4:
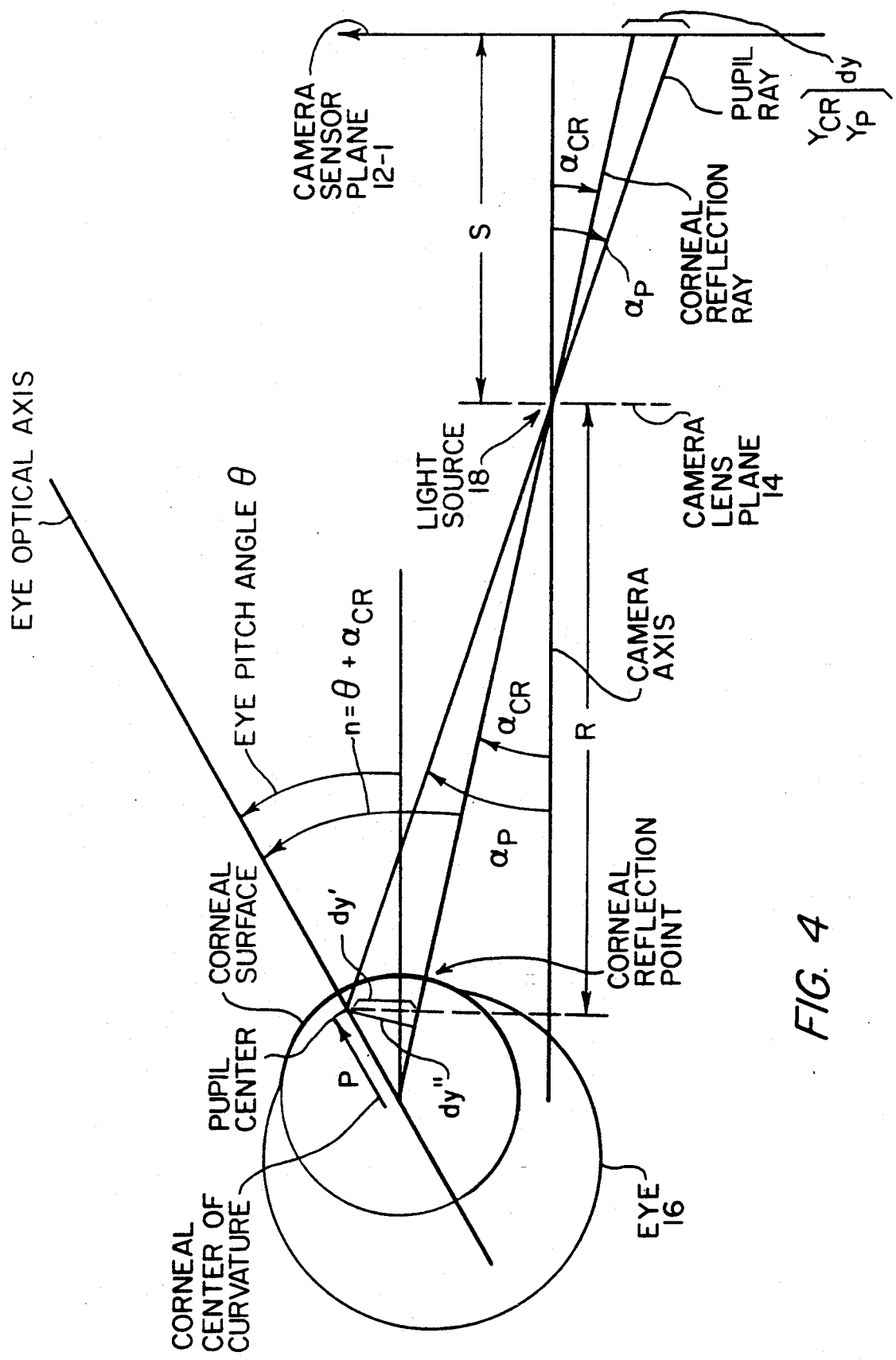
FIG. 4 shows a side view of a typical configuration of an eye orientation geometry.
Figure 5:
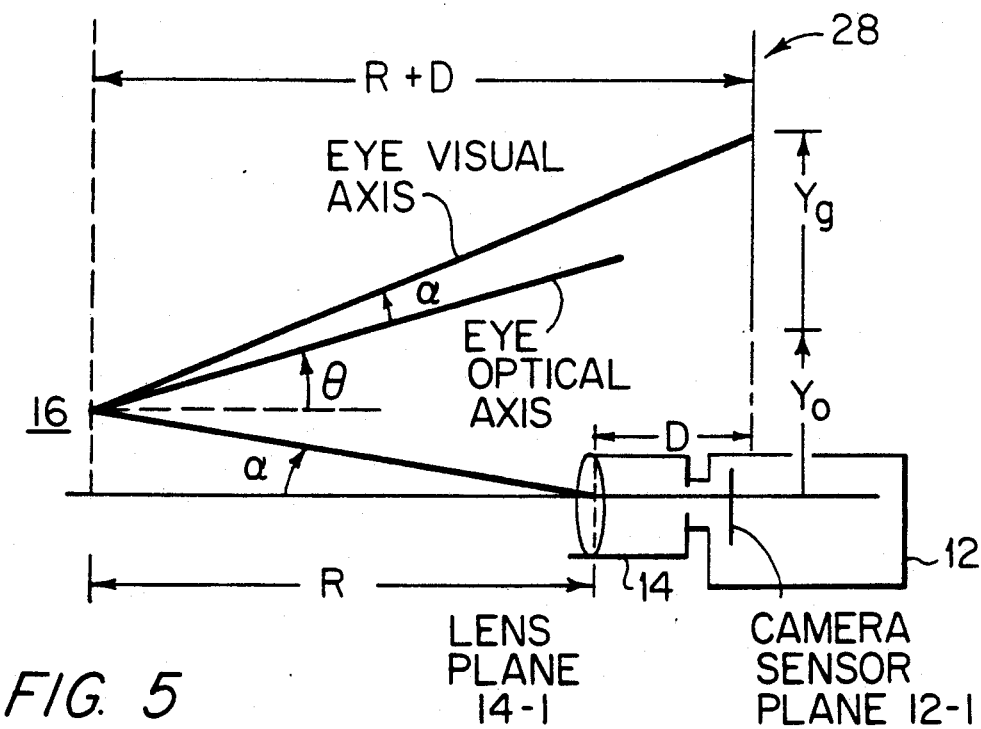
FIG. 5 shows a side view of a geometry for gaze point projection.

As described above, a common method in the image processing field for finding an object known to be either brighter or darker than its background is to set an intensity threshold value somewhere between the intensities of the object and its background and to search the image for a contour of pixels whose intensity crosses the threshold. See K. R. Castleman, "Digital Image Processing," Prentice-Hall, Englewood Cliffs, NJ (1979) and W. K. Pratt, "Digital Image Processing," John Wiley & Sons, New York (1978). The amplitude threshold crossing method is often used in processing eye images to locate the pupil and the corneal reflection. Since the corneal reflection is generally the highest anywhere in the region of the iris, the threshold for detecting the corneal reflection is generally set to a value just greater than the average pupil intensity, and the threshold for detecting the pupil is generally set to a value about midway between the average iris intensity and the average pupil intensity, assuming that the bright-eye effect is used.

Several problems typically arise when using the amplitude threshold crossing method to locate image features such as the pupil and corneal reflections. First, the accuracy of the feature position is limited to integer pixel values. Second, if the pixel intensity gradient across the feature edge is not particularly steep, small changes to the threshold value may result in significant changes in the detected edge position. Third, if there is significant noise in the intensity profile, there may be several threshold transitions in the vicinity of the edge and the detected edge position therefore becomes ambiguous. Finally, if the intensities of the feature image and its background vary significantly at different points around the edge contour, the detected edge position may shift toward or away from the true edge position.

As described above, a central goal in most eye monitoring applications is to measure the orientation of the eye with as much accuracy as possible. As can be seen from the approximations for the eye orientation angles, the accuracy of the orientation calculations is directly dependent on the accuracy of the measurements of the centers of the pupil and the corneal reflection.

In a typical eye monitoring application where a person sits in front of a computer monitor at a range of about 16–22 inches from the monitor screen and about 18–24 inches from the camera mounted below the screen and where the camera has a 75 millimeter lens, the image of the pupil will be on the order of 25 pixels across, and the position of the corneal reflection will typically move through a range of about 20 pixels, with respect to the center of the pupil, as the person scans the typical 10 inches from one side of the monitor screen to the other. If an objective of the system is to allow the user such as a physically disabled person to type with his eyes by gazing at individual keys represented on the display screen by icons whose sizes are ⅜ inch square, it is required to resolve the user's gaze point with better than a quarter-inch accuracy on the display screen if reliable system performance is to be achieved. Thus, given a 20 pixel range of the pupil-center/corneal-reflection vector and a screen dimension of 25 quarters of an inch the eye monitoring system must resolve the pupil-center/corneal reflection vector with better than 0.8 pixel accuracy. Because noise on both the pupil center and corneal reflection position measurements add when computing the pupil-center/-corneal-reflection vector's magnitude, the design requirements for pupil center and corneal reflection location accuracies are on the order of half a pixel. Since the pupil center coordinate is the average of edge measurements on opposite sides of the pupil, and noise from the two measurements is again additive, the required accuracy of pupil edge measurements is approximately a quarter pixel. As described above, such accuracy is difficult to achieve when the gaze-point is to be calculated at a video frame rate or better.

The above described amplitude threshold crossing method using "equal-weighting" locates the center of the corneal reflection as a simple average of the x and y coordinates of all pixels whose intensities exceed the corneal reflection threshold $T_{cr}$. If positive noise happens to push a pixel intensity from a value just below the threshold to a value just above the threshold, the weight that the pixel has in determining the estimate of the corneal reflection center switches abruptly from zero to a value equal to that of any other pixel whose intensity exceeds the threshold. Similarly, if negative noise pushes a pixel intensity below the threshold its weight abruptly vanishes. Since the number of pixels exceeding the corneal reflection threshold is typically small, the coarse quantum changes in the weights can have significant effect on the corneal reflection position estimate.

Figure 6A:
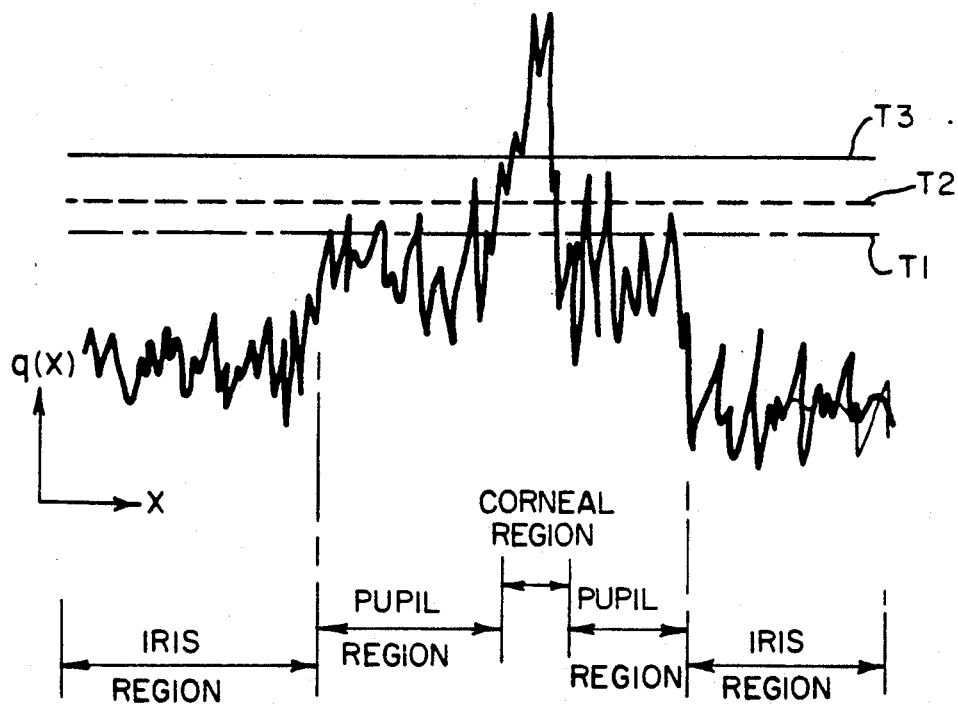
FIGS. 6a and 6b show unsmoothed and smoothed image intensity profiles.

In measuring the center of the corneal reflection, it is often desired to set the threshold $T_{cr}$ as low as possible with respect to the background signal so as to make use of as much light from the corneal reflection as possible. One of the problems with measuring the corneal reflection center with the equal-weighting method is that the amplitude detection threshold $T_{cr}$ must also be set fairly high so that noise in the background pupil or iris regions does not significantly disturb the corneal reflection center measurement. FIG. 6a shows a profile of the image intensity taken through a cross section of the eye's iris, pupil (illuminated using the bright-eye effect) and the corneal reflection. Using the equal-weighting method, the threshold should be set at the uppermost value T3 of the three values T1–T3 so that the corneal reflection position computation will not be adversely affected by the two noise spikes in the pupil region to the right of the corneal reflection.

In accordance with the present invention, a method that is less sensitive to noise includes application of selectable weights to the pixels whose intensities exceed the threshold. In general, the magnitudes of the weights increase monotonically with the magnitudes of the pixel intensities above the threshold: thus:

$$x_{cr} = \frac{\sum_{n=1}^{N} w_n x_n}{\sum_{n=1}^{N} w_n}$$

$$y_{cr} = \frac{\sum_{n=1}^{N} w_n y_n}{\sum_{n=1}^{N} w_n}$$

where $w_n$ are the weights.

One suitable weighting procedure is to make the magnitude of each pixel's weight proportional to the pixel's amplitude above the threshold:

$$w_n = q_n - T \text{ if } q_n \geq T$$

$$w_n = 0 \text{ if } q_n < T$$

where $q_n$ is the n-th pixel's intensity and T is the threshold value. Using this weighting procedure, the estimate of the corneal reflection center is often referred to as the first moment or the center of mass. Another monotonically increasing weighting procedure is to make the magnitude of each pixel's weight proportional to the square of the pixel's amplitude above the threshold. Other weighting procedures are also possible. These procedures can be referred to as the "center-of-mass" method.

Compared to the equal-weighting method, noise variations in the image intensity values have significantly less impact on the estimate of the corneal reflection center using the center-of-mass method. Referring again to FIG. 6a, if the value $T_{cr}$ of the corneal detection threshold is reduced to the middle value T2, a significantly greater portion of the corneal reflection light is used, better estimating the corneal reflection center. Furthermore, the impact of the noise spikes is minimal because their amplitudes above the threshold, hence their weights and contribution to the computation, are small. Thus, a key advantage of the center-of-mass method compared to the equal-weighting method is that the threshold value $T_{cr}$ may be lowered significantly before the effects of noise adversely affect the center measurement more than the reduction of the threshold improves it.

Figure 6B:
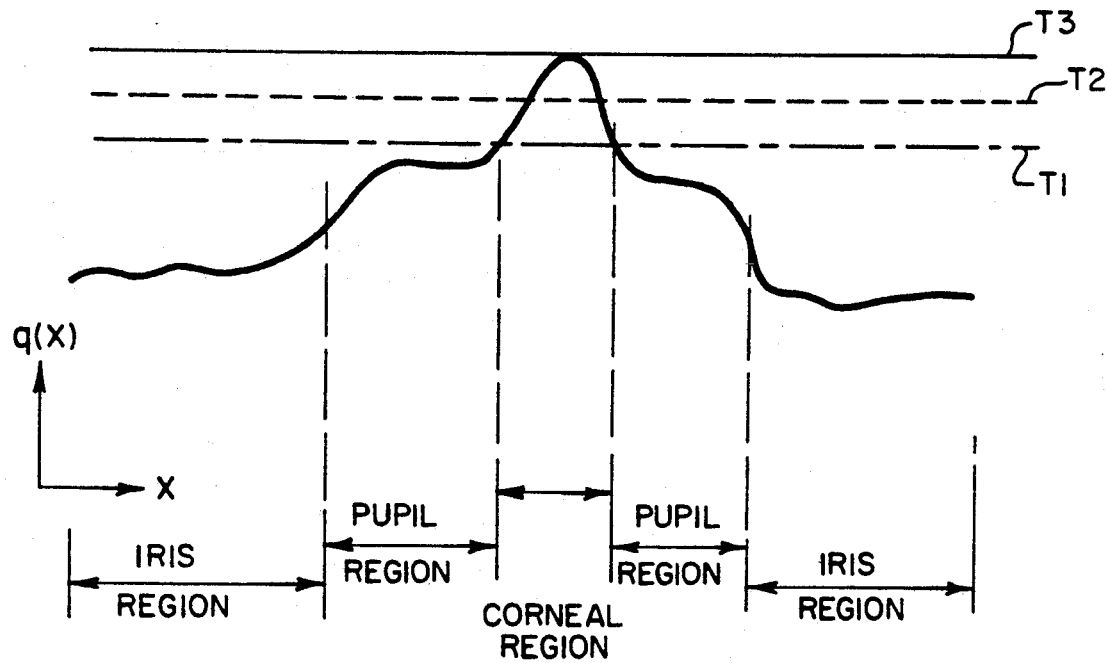

The corneal detection threshold $T_{cr}$ can be further reduced, and even more of the light reflected from the cornea used in the calculation of its center, by smoothing the intensity profile prior to the thresholding operation. FIG. 6b shows the curve of the intensity profile shown in FIG. 6a that has been smoothed. It can be seen from FIG. 6b that the threshold value $T_{cr}$ can be reduced to the lowest value T1 of the three shown values without the noise from the pupil region adversely affecting the estimate of the corneal reflection center. Accordingly, the best location accuracy can be obtained when the intensities of a 2-dimensional group of image pixels including the entire corneal reflection is smoothed, a low threshold value $T_{cr}$ selected just above the background intensity, and the center-of-mass method applied to the smoothed image intensity values exceeding the threshold.

In general, the threshold value $T_{cr}$ should be set at about the upper 2-standard-deviation level of the smoothed background intensity in the region surrounding the corneal reflection.

Suitable smoothing or low-pass filtering has the beneficial effect of reducing the magnitude of the image intensity noise, thereby reducing the number of pixels that exceed the detection threshold. Because the image is 2-dimensional, a suitable smoothing filter is also 2-dimensional, although a 1-dimensional filter can also be used.

A procedure for generating a smoothed image intensity profile $q_s(x_i, y_j)$ is:

$$q_s(x_i, y_j) = \sum_{k=-K}^{K} \sum_{m=-M}^{M} c_{k,m}\, q(x_{i+k}, y_{j+m})$$

where $c_{k,m}$ are coefficients of a convolution kernel, i.e., the smoothing filter, i and j are pixel indices, and k and m are relative offsets between unsmoothed and smoothed image pixel locations. It will be appreciated that the smoothing should be done with a convolution kernel symmetric about the k and m origins so as not to shift the smoothed image that could bias the estimate of the corneal reflection center. Suitable 2-dimensional, symmetric convolution kernels are illustrated in FIGS. 7A–7D.

It should be understood that although smoothing the intensity profile may appear to have the adverse effect of spreading out the image of the corneal reflection, thereby making it less distinct and harder to locate accurately, the operation of computing the corneal reflection center, either by the equal-weighting method or by the center-of-mass method, compensates for the spreading with its summation process.

Just as described above in relation to locating the corneal reflection, when using the amplitude threshold crossing method to locate an edge between the pupil and the background iris, it is important that the value of the pupil threshold $T_p$ be properly located between the iris and pupil intensities. If the average intensities of the pupil and iris vary as the orientation of the eye changes with respect to the camera and eye illuminator, or if the intensities of the pupil and iris change at different positions around the pupil, the pupil threshold value should be adapted accordingly.

In another aspect of the present invention, a method that is insensitive to the absolute intensities of the pupil and iris intensities involves first differentiating a 1-dimensional group of intensity samples that crosses the pupil edge to highlight the edge contour. The amplitude of the resulting differentiated edge signal is independent of the absolute level of the image intensity; it reflects only the relative difference between the pupil and iris intensities.

A mathematical representation of the differentiated pixels $dq(x_i)/dx$ is:

$$\frac{dq(x_i)}{dx} = \frac{q(x_i) - q(x_{i-1})}{x_i - (x_{i-1})}$$

where pixel intensities $q(x_i)$ are assumed taken along an axis x which can be any line in the image plane and i is an index for the pixels. It will be understood, however, that selecting the axis so that it is parallel to an axis of the pixel array will generally facilitate processing.

Figure 8A:
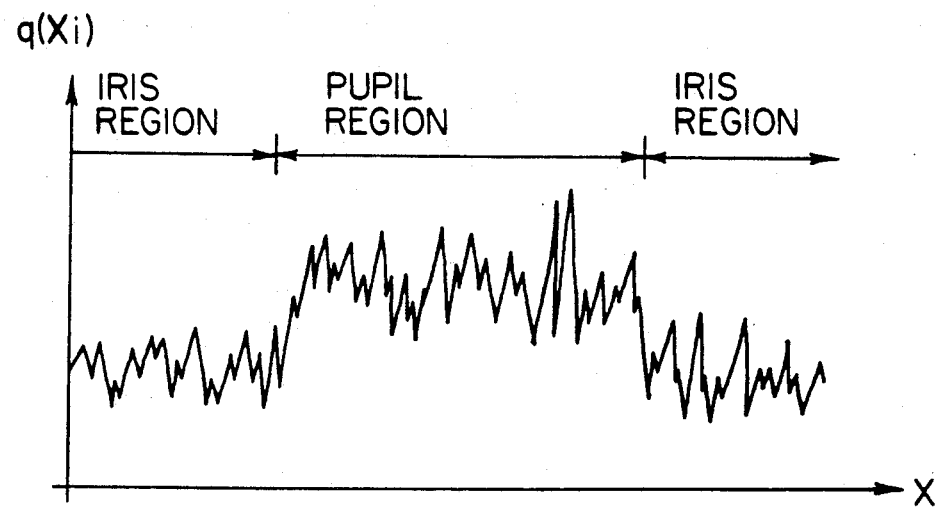
FIGS. 8A-8C show unprocessed and processed pupil image intensity profiles and ferentiating and smoothing.
Figure 8B:
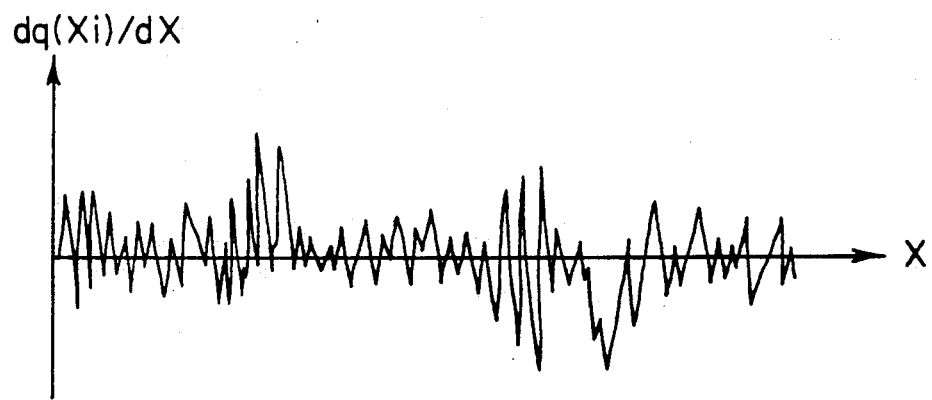

When there is a contrast between the pupil and the iris intensities, each differentiated edge will appear as a spike in the differentiated edge signal. Shown in FIG. 8A is an intensity profile taken through a pupil illuminated by the bright-eye effect. FIG. 8B represents a differentiation of the profile of FIG. 8A. It can be noted from FIG. 8B that because the intensity within the pupil is roughly constant and because the intensity within the iris is roughly constant, the average levels of the derivative within the pupil region and within the iris regions are about zero. Major peaks in the derivative curves occur at the transitions between the pupil and iris, and because the differentiated intensity signal is rising at one edge of the pupil and falling at the other, the polarities of the peaks for the left and right edges are different. For purposes of locating the edges, however, the polarities of both peaks can be interpreted as positive.

It will be appreciated that the spikes are significantly easier to detect with an amplitude thresholding procedure, and that the bipolar spikes arising from the pupil edges are simply discriminated from a bipolar derivative signal due to the corneal reflection by looking for two spikes of opposite polarity separated by more than the typical corneal reflection diameter.

The remainder of the procedure for detecting the location of the pupil edge is similar to that of locating the center of the corneal reflection. The key difference is that locating an edge coordinate involves searching for a peak signal along a 1-dimensional line through the image rather than searching for a peak in the 2-dimensional image plane to locate the center of the corneal reflection. Thus, smoothing and center calculations are 1-dimensional operations rather than 2-dimensional. It will be appreciated that the advantages of the corneal reflection center methods apply equally to the pupil edge detection methods.

Figure 9A:
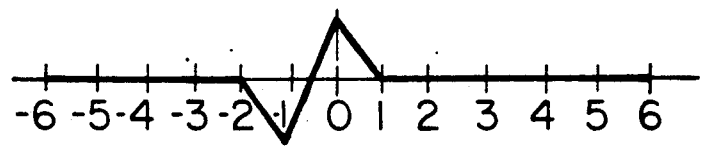
FIGS. 9A-9X show convolution kernels for image differentiating and smoothing.
Figure 9B:
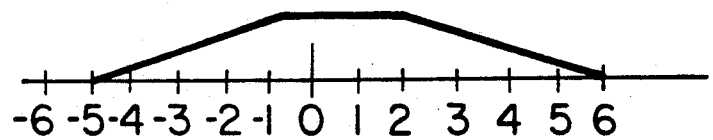
Figure 8C:
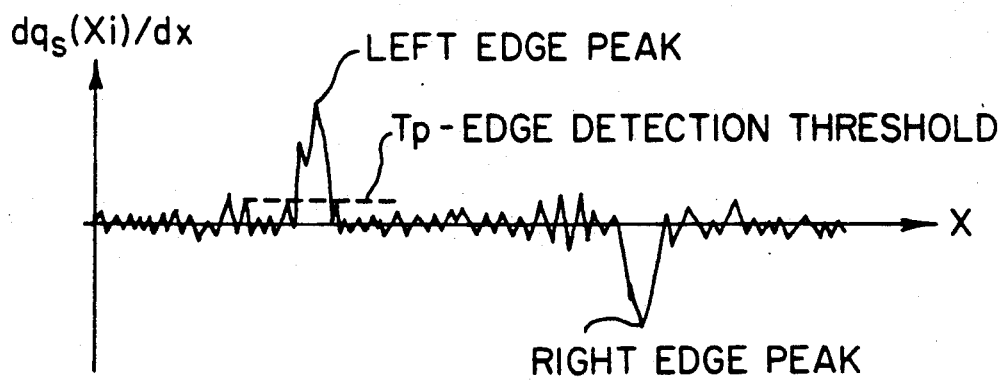

In locating an x coordinate of a pupil edge using the above described method, the smoothing operation is very important. The original intensity profile from the camera image (shown in FIG. 8A) generally contains a significant amount of high frequency noise, and the differentiation procedure amplifies that noise considerably. A smoothing operation prior to thresholding significantly reduces the effect of this noise on the center of mass calculation as shown in FIG. 8c. For good operation, the value $T_p$ of the pupil edge detection threshold should be set at about two standard deviations of the smoothed background intensity in the iris area around the pupil. An example of a suitable 1-dimensional smoothing kernel is shown in FIG. 9B. FIG. 9a shows a convolution kernel for carrying out the differentiation.

It will be understood that, due to the differencing of image samples, the above differentiation procedure results in a one-half pixel left-shift in the location of the derivative signal peaks with respect to the original intensity profile, and this left shift must be compensated when locating the pupil edge. One way to accommodate the left shift is to insert a one-half pixel right-shift in the smoothing operation, e.g., by using the kernel shown in FIG. 9B.

Figure 9C:
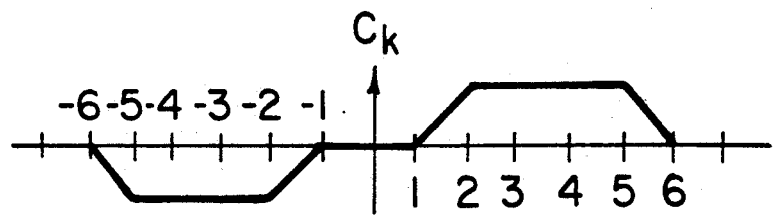

Because both the differentiation and smoothing operations are linear convolution processes, the sequence of these two operations is irrelevant. Furthermore, to save computing time, these two operations may be combined into a single linear convolution process. An example of a combined differentiation-smoothing kernel is shown in FIG. 9C. Note that the combined kernel for the differentiation smoothing operation is anti-symmetric about its origin, resulting in no set shift of the edge coordinates. It will be appreciated that the type of kernel used also depends on the image resolution, i.e., the number of pixels that "see" the pupil edge. The kernel shown is suitable for the eyegaze tracking apparatus described above in which the pupil edge is "seen" by about three to five pixels.

It will be understood that the invention has been described illustratively, not restrictively. Those of ordinary skill in the art will recognize various modifications and embodiments that do not depart from the spirit and scope of the invention which is to be limited only by the following claims.

What is claimed is:

1. A computerized method for locating a corneal reflection within an image of an eye comprising the steps of:
   illuminating the eye with a light source to produce light reflected by the eye;
   using a camera to convert the light reflected by the eye into a two-dimensional image of at least a portion of the eye, said image including a corneal reflection;
   converting a segment of the image representative of the corneal reflection into a sequence of gray scale reflection data;
   thresholding the gray scale reflection data by subtracting a predetermined threshold value from each element of the sequence to find the magnitudes of intensities above the threshold;
   scaling the thresholded corneal reflection data according to a monotonic scale prior to finding the center of mass; and
   locating the corneal reflection by finding a center of mass of the scaled thresholded data.

2. The computerized method as set forth in claim 1, further comprising the step of smoothing the collected data prior to thresholding.

3. An apparatus for locating a corneal reflection within an image of an eye comprising:
   a light source illuminating the eye to produce light reflected by the eye;
   a camera capturing light reflected by the eye to produce a two-dimensional image of at least a portion of the eye, said image including a corneal reflection;
   means for converting a segment of the image representative of the corneal reflection into a sequence of gray scale reflection data;
   means for thresholding the gray scale reflection data by subtracting a predetermined threshold value from each element of the sequence to find the magnitude of the intensities above the threshold;
   means for scaling the thresholded corneal reflection data according to a monotonic scale prior to finding the center of mass; and
   means for locating the corneal reflection by finding a center of mass of the scaled thresholded data.

4. The apparatus as set forth in claim 3, further comprising means for smoothing the collected sequence of gray scale data prior to thresholding.

5. A computerized method for locating an edge feature within an image of an object comprising the steps of:
   illuminating the object with a light source to produce light reflected by the object;
   using a camera to convert light reflected by the object into a two-dimensional image of at least a portion of the object, said image including the edge feature;
   converting a segment of the image representative of the edge feature into a sequence of gray scale reflection data;
   emphasizing the edge feature by spatially differentiating the sequence of gray scale reflection data to obtain a sequence of emphasized derivative data;
   thresholding the emphasized derivative data by subtracting a predetermined threshold value from each element of the sequence to find the magnitudes of the data above the threshold; and
   locating the edge feature by finding a center of mass of the thresholded emphasized derivative data, wherein the center of mass is obtained by the application of selected weights to the image coordinates, and wherein the selected weight at each image coordinate increases monotonically with the thresholded emphasized data for that coordinate.

6. The computerized method as set forth in claim 5, further comprising the step of smoothing the emphasized derivative data prior to thresholding.

7. The computerized method as set forth in claim 5, wherein the image is that of an eye and the edge feature is an edge feature of one of a pupil and iris of said eye.

8. The computerized method as set forth in claim 6, wherein the image is that of an eye and the edge feature is an edge feature of one of a pupil and iris of said eye.

9. A computerized method for locating a corneal reflection within an image of an eye comprising the steps of:
   illuminating the eye with a light source to produce light reflected by the eye;
   using a camera to convert the light reflected by the eye into a two-dimensional image of at least a portion of the eye, said image including a corneal reflection;
   converting a segment of the image representative of the corneal reflection into a sequence of gray scale reflection data;
   thresholding the gray scale reflection data by subtracting a predetermined threshold value from each element of the sequence to find the magnitude of intensities above the threshold; and
   locating the corneal reflection by finding a center of mass of the thresholded data, wherein the center of mass is obtained by the application of selected weights to the image coordinates, and wherein the selected weight at each image coordinate increases monotonically with the thresholded data for that coordinate.

10. The computerized method as set forth in claim 9, further comprising the step of smoothing the collected data prior to thresholding.

11. The computerized method as set forth in claim 9, further comprising the step of scaling the thresholded data according to a monotonic scale prior to finding the center of mass.

12. An apparatus for locating an edge feature within an image of an object comprising:
   a light source illuminating the object to produce light reflected by the object;
   a camera capturing light reflected by the object to produce a two-dimensional image of at least a portion of the object, said image including the edge feature;
   means for converting a segment of the image representative of the edge feature into a sequence of gray scale reflection data;
   means for emphasizing the edge feature by spatially differentiating the sequence of gray reflection scale data to obtain a sequence of emphasized derivative data;
   means for thresholding the emphasized derivative data by subtracting a predetermined threshold value from each element of the sequence to find the magnitudes of the emphasized data above the threshold; and
   means for locating the edge feature by finding a center of mass of the thresholded emphasized data, wherein the center of mass is obtained by the application of selected weights to the image coordinates, and wherein the selected weight at each image coordinate increases monotonically with the thresholded emphasized data for that coordinate.

13. The method as set forth in claim 12, further comprising the step of smoothing the emphasized derivative data prior to thresholding.

14. The method as set forth in claim 12, wherein the image is that of an eye and the edge feature is an edge feature of one of a pupil and iris of said eye.

15. The method as set forth in claim 12, wherein the image is that of an eye and the edge feature is an edge feature of one of a pupil and iris of said eye.

16. An apparatus for locating corneal reflection within an image of an eye comprising:
   a light source illuminating the eye to produce light reflected by the eye;
   a camera capturing light reflected by the eye to produce a two-dimensional image of at least a portion of the eye, said image including a corneal reflection;
   means for converting a segment of the image representative of the corneal reflection into a sequence of gray scale reflection data;
   means for threshodling the gray scale reflection data by subtracting a predetermined threshold value from each element of the sequence to find the magnitude of the intensities above the threshold; and
   means for locating the corneal reflection by finding a center of mass of the thresholded data, wherein the center of mass is obtained by the application of selected weights to the image coordinates, and wherein the selected weight at each image coordinate increases monotonically with the thresholded data for that coordinate.

17. The apparatus as set forth in claim 16, further comprising means for smoothing the collected sequence of gray scale data prior to thresholding.

18. The apparatus as set forth in claim 16, further comprising means for scaling the thresholded data according to a monotonic scale prior to finding the center of mass.

* * * * *